United States Patent [19]
Dusek et al.

[11] Patent Number: 5,176,701
[45] Date of Patent: Jan. 5, 1993

[54] MEDICAL FORCEPS INSTRUMENT FOR IMPLANTING INTRAOCULAR LENSES

[76] Inventors: Jarmila Dusek; Vaclav Dusek, both of 6210 Lake Washington Blvd., Renton, Wash. 98056

[21] Appl. No.: 702,791

[22] Filed: May 17, 1991

Related U.S. Application Data

[63] Continuation-in-part of Ser. No. 446,650, Dec. 6, 1989, abandoned, which is a continuation of Ser. No. 200,043, May 27, 1988, abandoned.

[51] Int. Cl.⁵ .............................. A61B 17/28
[52] U.S. Cl. ..................... 606/207; 606/205; 606/206; 606/210; 606/107; 294/99.2
[58] Field of Search ............... 606/107, 205, 206, 207, 606/210, 211; 433/159; 294/99.2; 81/418, 420; D28/55

[56] References Cited

U.S. PATENT DOCUMENTS

| | | | |
|---|---|---|---|
| D. 195,931 | 8/1963 | Chernov | D83/12 |
| D. 275,790 | 10/1984 | Marlowe | D24/27 |
| 1,386,436 | 8/1921 | Smith | |
| 1,837,277 | 12/1931 | Lund | |
| 3,306,139 | 2/1967 | Brackett | 81/43 |
| 3,364,933 | 1/1968 | Leopold | 128/321 |
| 3,489,151 | 1/1970 | Eller | 128/356 |
| 3,496,807 | 2/1970 | Jones et al. | 294/99.2 |
| 3,741,602 | 6/1973 | Ploeckelmann | 294/99.2 |
| 3,866,610 | 2/1975 | Kletschka | 128/322 |
| 3,916,910 | 11/1975 | Seeling et al. | 128/354 |
| 3,952,749 | 4/1976 | Fridolph et al. | 128/321 |
| 4,143,427 | 3/1979 | Anis | 3/13 |
| 4,226,240 | 10/1980 | Walker, Jr. | 128/321 |
| 4,226,241 | 10/1980 | Walker, Jr. | 128/321 |
| 4,325,375 | 4/1982 | Nevy | 128/321 |
| 4,440,170 | 4/1984 | Golden et al. | 128/325 |
| 4,461,283 | 6/1987 | Holskin et al. | 128/354 |
| 4,686,980 | 8/1987 | Williams et al. | 128/303.13 |

FOREIGN PATENT DOCUMENTS

| | | | |
|---|---|---|---|
| 2529955 | 1/1977 | Fed. Rep. of Germany | 294/99.2 |
| 1323089 | 7/1987 | U.S.S.R. | |
| 2073086 | 10/1981 | United Kingdom | |

*Primary Examiner*—Michael H. Thaler
*Attorney, Agent, or Firm*—Christensen, O'Connor, Johnson & Kindness

[57] ABSTRACT

Elongated generally horizontal blades are spaced apart vertically and have proximate handle end portions and distal grasping end portions. By manipulation of the handle end portions, the grasping end portions can be brought together into clamping engagement. The lower grasping end portion is return bent and includes a marginal portion offset laterally from the remainder of the lower blade. The upper grasping end portion is movable downward alongside the lower blade so as to engage against such laterally offset marginal portion of the lower grasping end portion. The composite forceps-type instrument is useful for implanting intraocular lenses during cataract surgery, particularly for positioning the superior haptic of an intraocular lens in a lens capsule.

22 Claims, 4 Drawing Sheets

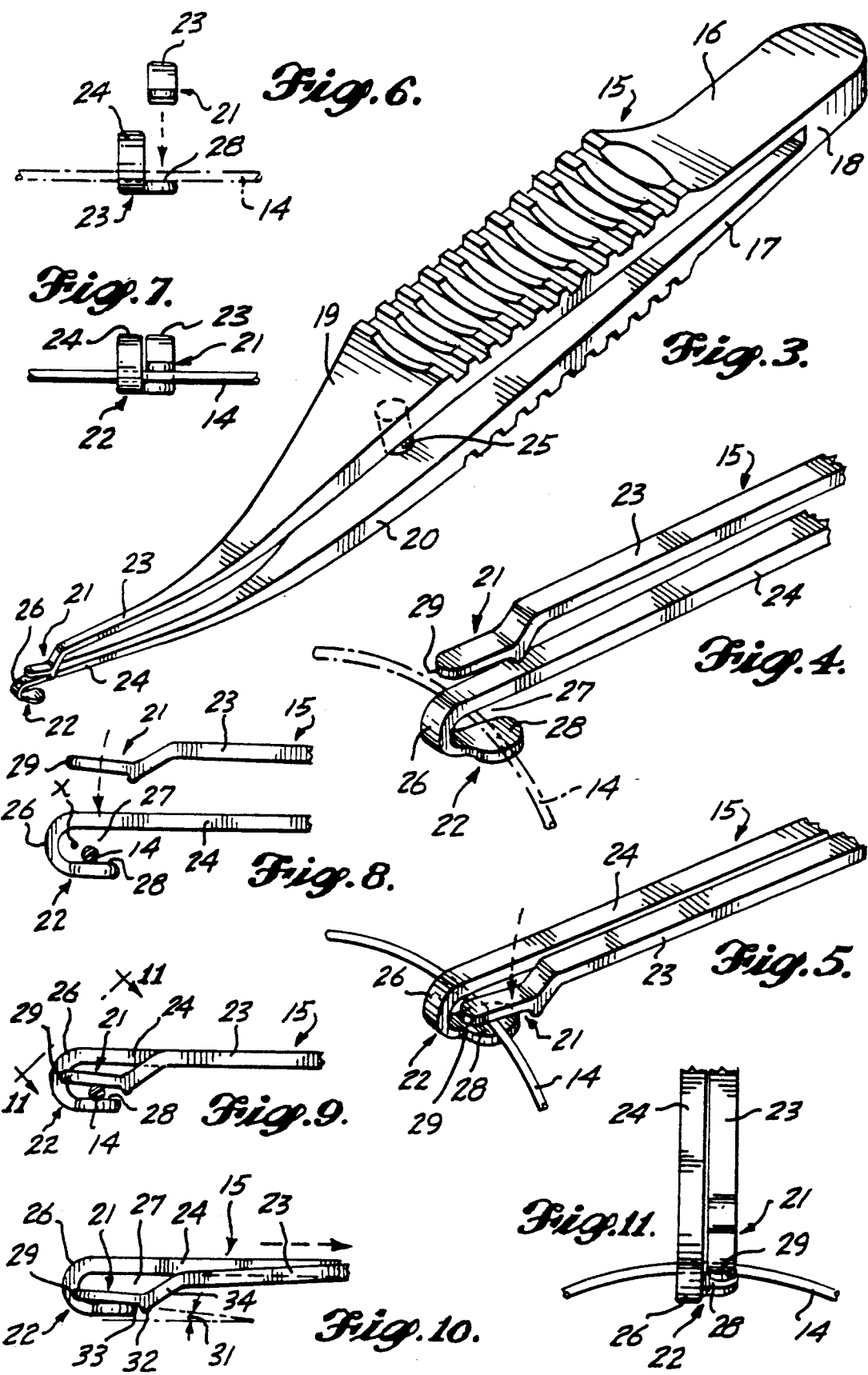

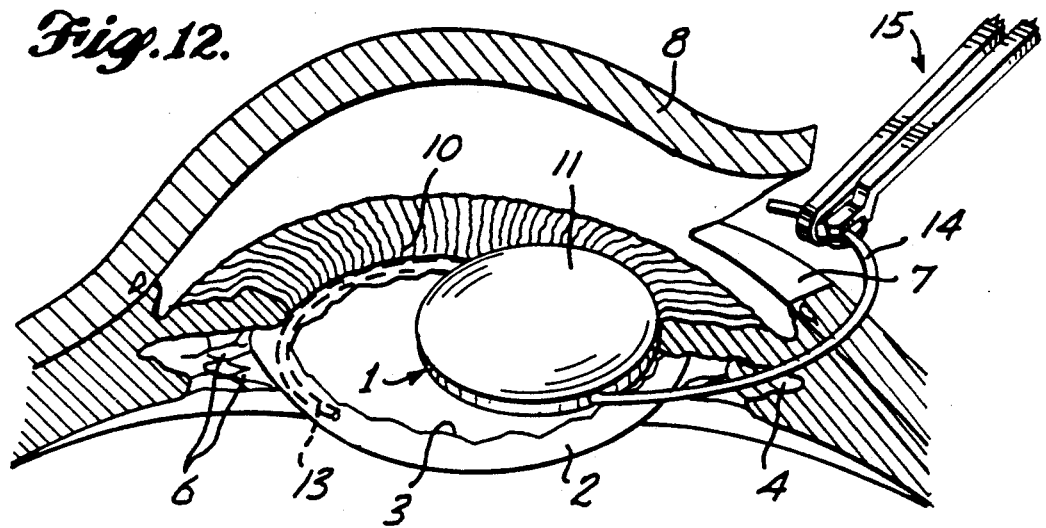
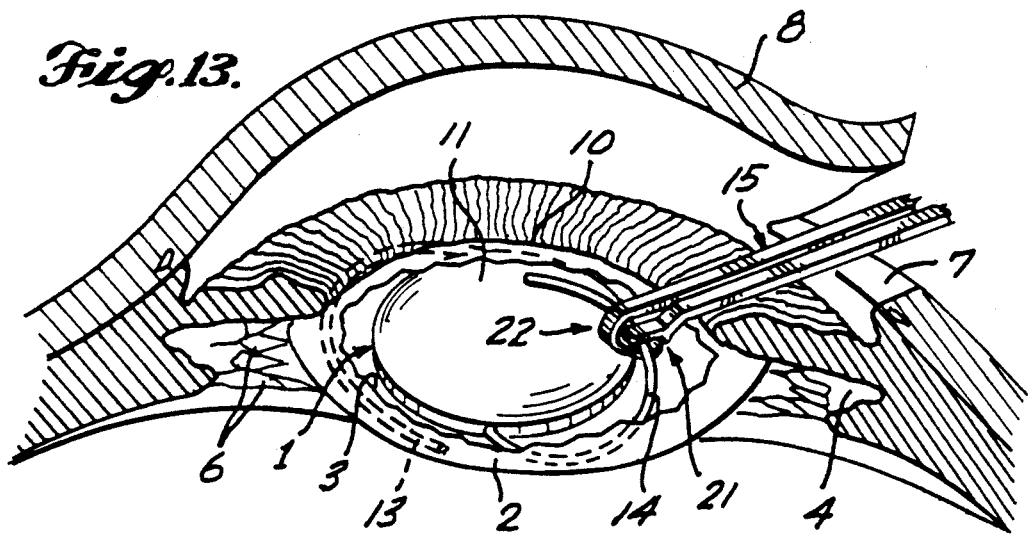
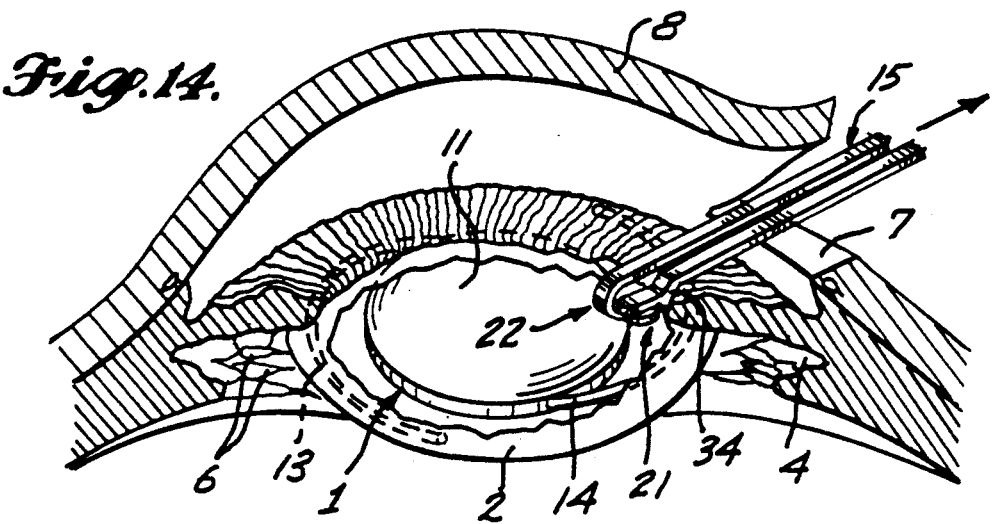

MEDICAL FORCEPS INSTRUMENT FOR IMPLANTING INTRAOCULAR LENSES

CROSS-REFERENCE

This application is a continuation-in-part of copending U.S. application Ser. No. 07/446,650, filed Dec. 6, 1989, in the name of Jarmila Dusek for Instrument for Implanting Intraocular Lens, abandoned as of the filing date accorded this application, which was a continuation of U.S. application Ser. No. 07/200,043, filed May 27, 1988, in the name of Jarmila Dusek for Instrument for Implanting Intraocular Lens, now abandoned. Both of such earlier applications are expressly incorporated by reference herein.

BACKGROUND OF THE INVENTION

1. Field of the Invention

The present invention relates to a forceps-type medical instrument used during cataract surgery for insertion of an artificial lens in an otherwise natural eye.

2. Prior Art

Moving from the exterior toward the center, a human eye includes the cornea, anterior chamber behind the cornea, iris, posterior chamber behind the iris and vitreous body which encompasses the major portion of the volume of the eyeball. The lens is located in the posterior chamber between the iris and the vitreous and consists of a relatively hard central nucleus surrounded by the softer cortex enclosed in a membrane called the capsule. The capsule and lens structure are held in position centered behind the iris by fibers called zonules that extend between the lens capsule and the periphery of the posterior chamber.

In modern cataract surgery, a short incision is made along the margin of the cornea for access to the lens through the central opening of the iris (pupil). The lens capsule is opened adjacent to the iris and the cloudy natural lens is removed. Preferably, the posterior portion of the lens capsule is left intact so that the posterior chamber remains isolated from the vitreous. Also, the zonules are not disturbed so that the opened lens capsule continues to be supported in the posterior chamber.

In a popular form of cataract surgery, an artificial intraocular lens is implanted after the natural lens has been removed. The intraocular lens includes a clear central optical portion intended to function the same as the clear natural lens of an undamaged and undiseased eye. The intraocular lens is designed to be centered in the posterior chamber. In a common form of intraocular lens, two thin, flexible but slightly resilient filaments called haptics are spiraled tangentially outward from opposite sides of the optical portion of the intraocular lens. The entire artificial lens structure is preferably implanted in the natural lens capsule. The haptics engage against the inner periphery of the capsule and, like weak leaf springs, gently support the optical portion of the artificial lens centered behind the iris.

The implant procedure involves grasping an edge portion of the central optical portion of the artificial lens by lens insertion forceps at a location generally opposite the location where one of the haptics extends. By manipulation of the forceps, such opposite haptic (the inferior haptic) is inserted into the lens capsule through the anterior opening made when the natural lens was removed. The optical portion of the intraocular lens is carefully inserted at least partway into the capsule leaving the trailing haptic (superior haptic) projecting from the capsule. Next, the optical portion of the lens is released and, in accordance with the known procedure, the same forceps are used to grasp the superior haptic and move it past the iris into the posterior chamber. The object is to position the superior haptic such that, when released, it will slowly and gently spring away from the optical portion of the lens and engage inside the lens capsule.

The implant procedure, of course, must be conducted with care because of the delicate nature of the surrounding tissue and the small work space provided by the corneal incision and pupil, but it can be difficult by use of known forceps to position the superior haptic within the natural lens capsule. It is not uncommon for the superior haptic to remain between the jaws of the forceps when released or to deploy outside the capsule, necessitating additional attempts to position the superior haptic properly. Such additional attempts can be irritating to the delicate eye tissue in addition to being frustrating and irritating to the surgeon. There also is the possibility that improper deployment of the superior haptic will not be detected during surgery which can result in the lens decentration and consequently in poor optical performance of the intraocular lens because it is not supported in the lens capsule as intended.

SUMMARY OF THE INVENTION

The present invention provides a medical forceps instrument including two horizontally elongated blades having proximate handle end portions and distal grasping end portions. The grasping end portions are normally spaced apart vertically, but the two blades are connected together such that manipulation of the handle end portions allows the grasping end portions to be brought into clamping engagement. The lower grasping end portion has a bend of substantially return bend configuration so as to form a grasping surface facing the underside of the remainder of its blade. The upper grasping end portion has a grasping surface on its underside which is movable downward into clamping engagement with the first grasping surface. The improved forceps are particularly useful for grasping the superior haptic of an intraocular lens and tucking such haptic through the pupil into the lens capsule. When the haptic is released, it springs free of the lower return bent grasping end portion and is reliably deployed in the lens capsule with no tendency to be pulled out of the lens capsule when the forceps are removed.

BRIEF DESCRIPTION OF THE DRAWINGS

FIG. 3 is an enlarged top perspective of the preferred form of medical forceps instrument for implanting intraocular lenses in accordance with the present invention.

FIG. 4 and FIG. 5 are further enlarged fragmentary top perspectives of an end portion of the instrument of FIG. 3 with parts in different positions; FIG. 6 and FIG. 7 are corresponding enlarged fragmentary front end elevations of an end portion of the instrument of FIG. 3 with parts in different positions; and FIG. 8, FIG. 9 and FIG. 10 are corresponding enlarged fragmentary side elevations of an end portion of the instrument of FIG. 3 with parts in different positions.

FIG. 11 is an enlarged fragmentary perspective of an end portion of the preferred instrument in accordance with the present invention taken from line 11—11 of FIG. 9.

FIG. 12, FIG. 13 and FIG. 14 are corresponding sectional views of an eye illustrating implantation of an intraocular lens by use of the preferred instrument in accordance with the present invention.

DETAILED DESCRIPTION

Figure 1:
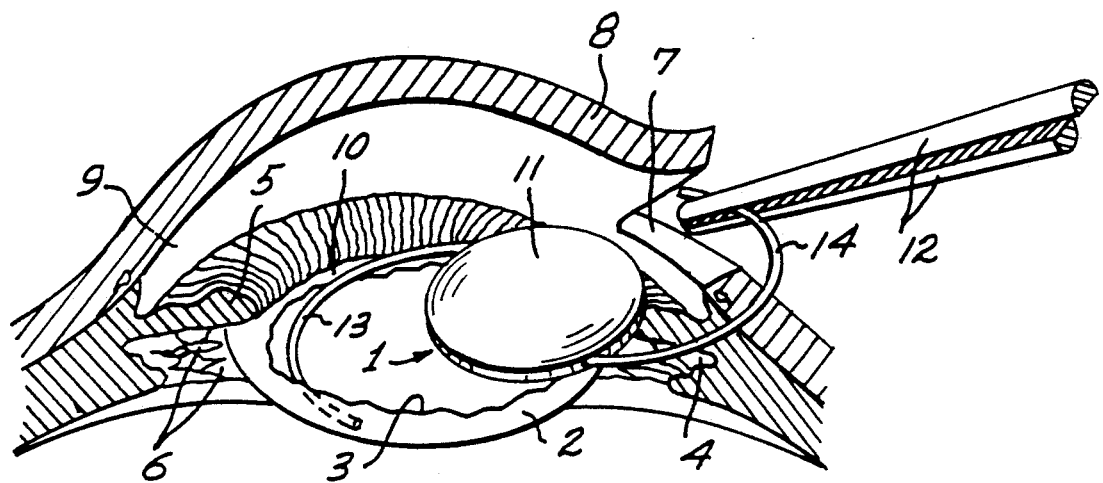
FIG. 1 and FIG. 2 are corresponding enlarged sectional views of an eye illustrating implantation of an intraocular lens by use of forceps of prior art design.
Figure 2:
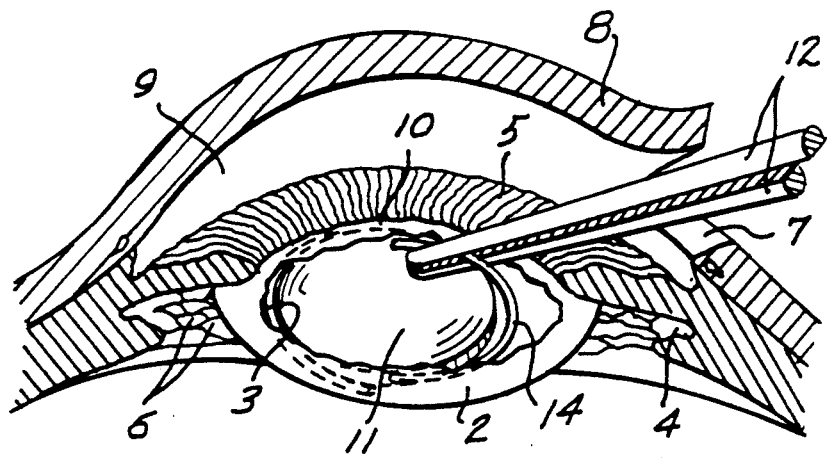

FIG. 1 and FIG. 2 illustrate part of the procedure of implanting an intraocular lens 1 into a natural lens capsule 2 from which the natural lens has been extracted. The extraction procedure leaves an anterior opening 3, but the remainder of the lens capsule is left intact supported in the posterior chamber 4 behind the iris 5 by the fibrous zonules 6. The extraction and implantation procedure is accomplished through a small incision 7 in the margin of the cornea 8 providing access through the anterior chamber 9 and pupil 10 to the anterior opening 3 of the lens capsule.

After cataract extraction, the optical central portion 11 of the intraocular lens is grasped between the directly opposed elongated jaws 12 of standard lens insertion forceps and is carefully manipulated to insert the inferior haptic 13 into the side of the lens capsule 2 opposite the incision 7 in the cornea. Inward movement of the intraocular lens is continued until its optical portion is inserted at least partway into the capsule. Thereafter, the optical portion of the intraocular lens is released and the superior haptic 14 is grasped between the jaws 12 of the forceps. The superior haptic is carefully manipulated so as to implant the optical portion of the lens all the way into the capsule 2.

A problem with the prior procedure is readily apparent from FIG. 2. The superior haptic is grasped between the elongated directly opposed forceps jaws 12 which extend through the small corneal incision 7 and through the pupil 10. Some rubbing engagement with the iris 5 is inevitable. From the position of FIG. 2, it is difficult to move the superior haptic 14 downward without unduly stretching the corneal incision 7 which could result in a tear. Also, if the superior haptic 14 is released from the position of FIG. 2 by spreading the jaws 12 apart slightly, the haptic will tend to slide along the jaws which creates the possibility of dislodging the haptic from the lens capsule 2 when the jaws are removed. Another possibility is for the superior haptic 14 to uncoil from the jaws and deploy outside the lens capsule 2 (which may be more or less collapsed after removal of the natural lens) into the periphery of the posterior chamber 4. It is desirable for such improper deployment to be detected during surgery so that additional attempts can be made to correct it. Nevertheless, such additional attempts inevitably cause further trauma to the tender tissue engaged by the forceps. If improper deployment is not detected, the implanted intraocular lens is not supported by both haptics in the lens capsule 2 as intended and the optical portion of the lens is decentered which results in poor optical performance.

The preferred embodiment of instrument 15 in accordance with the present invention shown in FIGS. 3 through 11 allows safe, easy, reliable and predictable positioning of the superior haptic in the lens capsule. Such instrument includes an upper horizontally elongated blade 16 and a lower horizontally elongated blade 17. Such blades are formed of resilient stainless steel and are integrally joined together at one end 18 (the handle end) of the instrument. The blades 16 and 17 have long directly opposed handle portions 19 and 20, respectively, extending forward or distally from end 18 and small grasping end portions 21 (upper blade) and 22 (lower blade). The grasping end portions 21 and 22 are connected to the corresponding handle portions 19 and 20 by narrow horizontal arms 23 and 24.

From the proximate or handle end 18 of the instrument, blades 16 and 17 gradually diverge vertically to approximately the longitudinal center of the instrument and from there gradually converge toward the grasping end portions 21 and 22. In the relaxed condition shown in FIG. 3, FIG. 4, FIG. 6 and FIG. 8, the grasping end portion 21 and arm 23 of the upper blade are higher than the grasping end portion 22 and arm 24 of the lower blade. As seen in FIGS. 5, 7, 9, 10 and 11, the grasping end portion 21 and arm 23 of the upper blade are offset laterally from the arm 24 of the lower blade. Consequently, by manually squeezing together the opposed handle portions 19 and 20 of the two blades, arm 23 is moved downward relative to arm 24 such that the grasping end portion 21 of the upper blade passes alongside and below arm 24 of the lower blade. The extent to which the handle portions of the two blades may be squeezed together is limited by a stop peg 25 projecting upward from the top surface of the bottom blade handle portion 20.

The grasping end portion 22 of the bottom blade is hooked or substantially return bent from its arm 24 about an axis X extending below and transversely of such arm so that the free end portion of grasping end portion 22 extends toward the handle, end of the instrument. Such return bent end portion forms a mouth 27 opening rearward, i.e., proximally toward the handle end of the instrument, with an upper, flat grasping surface 28 spaced below and facing the underside of the blade arm 24. Surface 28 has a marginal portion offset laterally from the lower blade arm 24 at the side along which the upper blade arm 23 extends. As seen in FIGS. 4, 5, 8, 9 and 10, the blunt return bend 26 of the grasping end portion 22 forms the most forward or distal end of the instrument 15.

The grasping end portion 21 of the upper blade extending from the arm 23 preferably has a rounded end 29 which extends forward or distally to a position which is still spaced rearward or proximate of the most forward or distal end of the lower blade grasping end portion 22. By squeezing together the handle portions of the two blades, grasping end portion 21 of the upper blade is moved relatively downward substantially perpendicular to axis X, such that its flat bottom or grasping surface adjacent to the rounded end 29 is substantially contiguously engageable against the top grasping surface 28 of the lower blade end portion 22, as best seen in FIG. 10. Preferably, the mating flat grasping surfaces are positioned at a very small acute angle 31 to horizontal when the linear upper blade arm 23 extends horizontally. In the preferred embodiment, such angle 31 is about 5 degrees and preferably is no greater than 30 degrees.

In the closed position indicated in FIG. 10, a downward-extending projection 32 of the grasping end portion 21 extends close alongside the rearward-facing end 33 of the grasping end portion 22. The bottom of such projection 32 preferably is approximately flush with the bottom of end portion 22. From there the top grasping end portion 21 is inclined upward and rearward to the support arm 23 such that the grasping end portion 21 closes the rearward-opening mouth 27 defined by the return bent grasping end portion 22 of the lower blade. In addition, the grasping surface of the upper blade formed on its underside is located substantially below the support arm 23.

FIGS. 4 and 5, FIGS. 6 and 7 and FIGS. 8 and 9 illustrate clamping of a superior haptic 14 by use of the preferred embodiment of instrument in accordance with the present invention. With the blades in their relaxed positions, the distal end portion of the instrument can be moved over the haptic, then downward and rearward such that the haptic moves through the mouth 27 formed by the grasping end portion 22 until the haptic is positioned over the flat grasping surface 28 of such end portion. The blades 16 and 17 are moved together to the positions indicated in FIGS. 5, 7, 9 and 11 such that the upper grasping end portion 21 moves downward relative to the lower grasping end portion 22 and alongside the arm 24. The haptic is grasped between the underside of the grasping end portion 21 and the portion of the underslung grasping end portion 22 which is laterally offset from its support arm 24.

FIGS. 12, 13 and 14 illustrate the advantage of the preferred form of instrument in accordance with the present invention for implanting an intraocular lens 1 in a lens capsule 2. After the inferior haptic 13 has been inserted into the lens capsule and the optical portion 11 has been inserted at least partway into the capsule, instrument 15 is used to grasp the central or trailing portion of the superior haptic 14, as described above and as shown in FIG. 12. As shown in FIG. 13, the instrument is moved substantially linearly inward through the corneal incision 7. The possibility of tissue damage or irritation is minimized because the blunt return bent end 26 of the lower blade is presented to adjacent tissue, as compared to the more sharply pointed ends of directly opposed jaws of standard forceps.

When the optical portion 11 of the intraocular lens has been positioned in the lens capsule 2 and the superior haptic 14 has been inserted through the pupil 10 and over the anterior capsule opening 3, as shown in FIG. 13, the distal end portion of the instrument 15 can be pressed or tilted gently downward such that the superior haptic 14 is tucked downward into the lens capsule. When the opposing handle portions of the instrument are released slightly so as to spread apart the grasping end portions 21 and 22 of the blades, the superior haptic gradually springs out from between the grasping surfaces toward the handle end of the instrument. Thus, the superior haptic moves freely out of the hooked grasping end portion 22 of the lower blade for engagement against the periphery of the lens capsule. Next, the blades can be brought together again such that the hooked end of the lower blade is closed. As illustrated in FIG. 14, with the grasping end portions 21 and 22 of the blades held together, the instrument is withdrawn lengthwise out through the corneal incision 7 without danger of the hooked end of the lower blade catching on delicate eye tissue. Rather, the smooth inclined portion 34 of the upper blade in combination with the flat tip of the blade closes the mouth of the hooked end of the lower blade and guides the instrument out of the eye. With reference to FIG. 10, the projection 32 of the upper blade grasping end portion 21 protects eye tissue from engagement against the thin end 33 of the grasping end portion 22.

Figure 15:
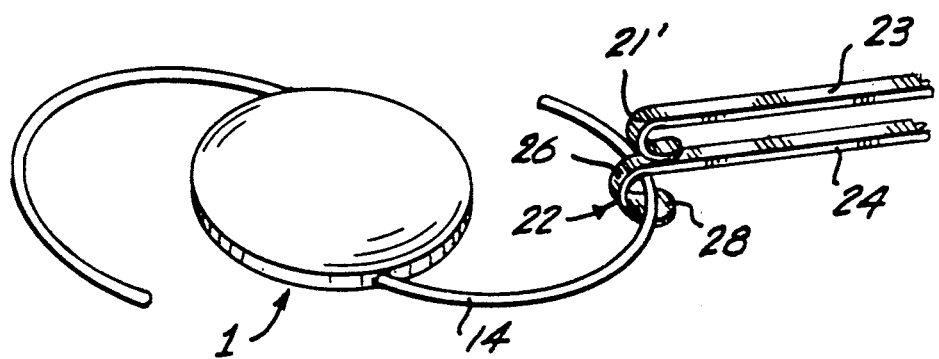
FIG. 15 and FIG. 16 are corresponding top perspectives of an intraocular lens and an end portion of a modified form of instrument in accordance with the present invention.
Figure 16:
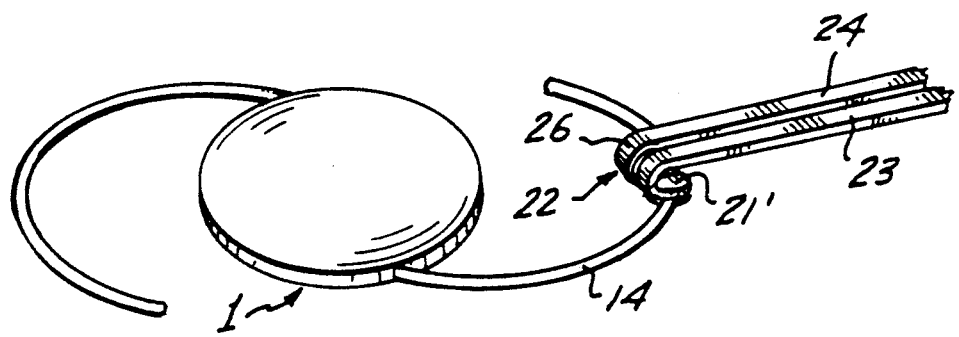

In the modified embodiment of the instrument in accordance with the present invention illustrated in FIGS. 15 and 16, the handle end portion (not shown) is identical to the handle end portion of the previously described embodiment including the opposed blade portions joined at the proximate end. Also, the lower blade including the return bent grasping end portion 22 and support arm 24 are the same as previously described. The blunt return bend 26 still forms the distal end of the instrument adjacent to the upward-facing grasping surface 28. Such surface includes a marginal portion offset laterally from the lower blade support arm 24. As in the previously described embodiment, arm 24 is offset laterally from the upper support arm 23 such that arm 23 is free to move downward past the lower arm 24 by squeezing the handle portions of the two blades together.

In the embodiment shown in FIGS. 15 and 16, however, the upper arm 23 supports a modified grasping end portion 21' which is return bent similar to grasping end portion 22 but which is of approximately the same width as the width of its support arm 23. As seen in FIG. 16, when the two blades are brought together, a haptic 14 of an intraocular lens 1 can be grasped between the underside of the return bent grasping surface 21' and the upward-facing grasping surface 28 of grasping end portion 22.

Use of the embodiment shown in FIGS. 15 and 16 is essentially the same as use of the previously described embodiment (shown in FIGS. 12, 13 and 14). The superior haptic can be easily tucked inside the lens capsule and, when the blades are released so that the grasping end portions spread apart slightly, such haptic is free to spring outward (rearward or proximally) from the hooked grasping end portion 22 of the lower blade. The surgeon must be somewhat more careful in removing the instrument from the eye, however, so that the hooked grasping portion of the upper blade does not catch on or irritate the delicate eye tissue.

Figure 17:
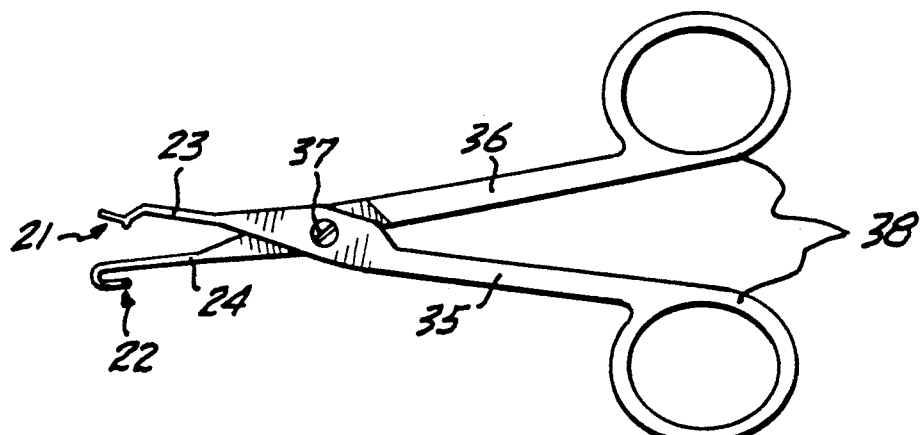
FIG. 17 is a side elevation of a further modified form of instrument in accordance with the present invention.

FIG. 17 illustrates another configuration for the instrument in accordance with the present invention. Grasping end portions 21 and 22 and laterally offset upper and lower support arms 23 and 24 are identical to the correspondingly numbered elements of the embodiment of FIGS. 3 through 14. In the embodiment of FIG. 17, however, arms 23 and 24 extend forward from longer handle blades or arms 35 and 36, respectively, which cross and are connected by a pivot 37. Finger loops 38 can be provided at the proximate ends of arms 35 and 36 for manipulating the blades to bring together and spread the grasping end portions 21 and 22. The effect is the same as for the embodiment of FIGS. 3 through 14, the only difference being that in the embodiment of FIG. 17 the pivot axis about which the clamping end portions swing relative to each other is closer to such clamping end portions than for the other embodiments. Otherwise, operation of the embodiment of FIG. 17 is identical to operation of the embodiment of FIGS. 3 through 14.

We claim:

1. In a medical forceps instrument including first and second generally horizontally elongated blades each having a proximate end, a handle end portion adjacent to said proximate end, a distal end and a grasping end portion adjacent to said distal end, the first blade having a lower generally horizontal elongated support arm carrying the grasping end portion of the first blade and extending therefrom to the handle end portion of the first blade, the second blade having an upper generally horizontal elongated support arm carrying the grasping end portion of the second blade and extending therefrom to the handle portion of the second blade, the lower support arm normally being disposed no higher than the upper support arm with the grasping end portions of the blades spaced apart but the first and second blades being connected such that their grasping end portions are movable together into clamping engagement by manipulation of the handle end portions of the blades, the improvement comprising the grasping end portion of the first blade having an underslung bend of substantially return bend configuration and a first grasping surface extending from said bend generally toward the handle end portion of the first blade, said first grasping surface facing upward toward the underside of the lower support arm, the grasping end portion of the second blade having a second grasping surface on the underside thereof movable into clamping engagement with said first grasping surface by manipulation of the handle end portions of the blades.

2. In the instrument defined in claim 1, the upper support arm being offset laterally from the lower support arm and being movable relatively downward past the lower support arm by manipulation of the handle end portions of the blades.

3. In the instrument defined in claim 1, the first and second grasping surfaces normally being directly opposed and spaced apart vertically, the second grasping surface being movable downward relative to the first grasping surface into clamping engagement therewith.

4. In the instrument defined in claim 3, the upper support arm being offset laterally from the lower support arm and being movable relatively downward past the lower support arm by manipulation of the handle end portions of the blades for bringing the first and second grasping surfaces into clamping engagement.

5. In the instrument defined in claim 4, the first grasping surface including a marginal portion offset laterally from the lower support arm at the side at which the upper support arm is offset laterally from the lower support arm, and the second grasping surface being positioned for engagement against said marginal portion.

6. In the instrument defined in claim 4, the proximate ends of the first and second blades being integrally joined together, said blades diverging gradually from their proximate ends to approximately their longitudinal centers and from there converging gradually toward their distal ends, said blades being formed of resilient material and, with the blades relaxed, the upper support arm and second grasping surface of the second blade being disposed higher than the lower support arm and first grasping surface of the first blade.

7. In the instrument defined in claim 4, the first and second blades being pivotally connected intermediate their proximate and distal ends.

8. In the instrument defined in claim 3, the distal end of the instrument being blunt and being formed by the bend of the grasping end portion of the first blade.

9. In the instrument defined in claim 3, the grasping end portion of the second blade including a portion inclined upward and proximally from the second grasping surface to the upper support arm when the first and second grasping surfaces are in engagement such that the second grasping surface is positioned substantially below the upper support arm.

10. In the instrument defined in claim 3, the grasping end portion of the first blade terminating in a free end facing the handle end portion of such blade, the grasping end portion of the second blade including a downward-extending projection positioned so as to lie close alongside and proximate said free end when the first and second grasping surfaces are in engagement.

11. In the instrument defined in claim 10, the grasping end portion of the second blade including a portion inclined upward and proximally from the second grasping surface to the upper support arm when the first and second grasping surfaces are in engagement such that the second grasping surface is positioned substantially below the upper support arm.

12. In the instrument defined in claim 3, the grasping surface of the second blade having a bend of substantially return bend configuration.

13. In the instrument defined in claim 3, the first and second grasping surfaces being flat and, when engaged, defining a small acute angle relative to the horizontal support arms.

14. In the instrument defined in claim 13, the angle being no greater than 30 degrees.

15. In the instrument defined in claim 13, the angle being about 5 degrees.

16. In a medical forceps instrument including first and second generally horizontally elongated blades each having a proximate end, a handle end portion adjacent to said proximate end, a distal end and a grasping end portion adjacent to said distal end, the first blade having a lower horizontal support arm carrying the grasping end portion of the first blade and extending therefrom to the handle end portion of the first blade, the second blade having an upper horizontal support arm carrying the grasping end portion of the second blade and extending therefrom to the handle portion of the second blade, the lower support arm normally being disposed no higher than the upper support arm with the grasping end portions of the blades spaced apart but the first and second blades being connected such that their grasping end portions are movable together into clamping engagement by manipulation of the handle end portions of the blades, the improvement comprising the grasping end portion of the first blade being hooked so as to form a mouth below the lower support arm which mouth opens proximally toward the handle end portion of the first blade and having a grasping surface in the lower portion of said mouth facing upward, the grasping end portion of the second blade having a grasping surface on the underside thereof movable into clamping engagement with said grasping surface of the first blade so as to close said mouth and being movable relatively away so as to open said mouth.

17. In the instrument defined in claim 16, the grasping surfaces normally being directly opposed and spaced apart vertically.

18. In the instrument defined in claim 17, the upper support arm being offset laterally from the lower support arm and being movable relatively downward past the lower support arm by manipulation of the handle end portions of the blades for bringing the grasping surfaces into clamping engagement.

19. In the instrument defined in claim 18, the grasping surface of the first blade including a marginal portion offset laterally from the lower support arm at the side at which the upper support arm is offset laterally from the lower support arm, and the grasping surface of the second blade being positioned for engagement against said marginal portion.

20. In a medical forceps instrument including first and second generally horizontally elongated blades each having a proximate end, a handle end portion adjacent to the proximate end, a distal end and a grasping end portion adjacent to the distal end, each of the blades having a generally horizontally elongated support arm carrying the grasping end portion of such blade and extending therefrom to the handle end portion of such blade, the improvement comprising the grasping end portion of the first blade having an underslung bend of substantially return bend configuration about an axis extending below and transversely of the support arm of such first blade and including a first grasping surface extending from said bend generally toward the handle end portion of the first blade, the grasping end portion of the second blade having a second grasping surface on the underside thereof, said first grasping surface of the first blade facing upward toward the underside of the grasping end portion of the second blade in vertical alignment with said second grasping surface, the first and second blades being connected such that their grasping end portions are relatively movable vertically substantially perpendicular to the axis of the underslung bend by manipulation of the handle end portions of the blades between a closed position in which the grasping surfaces are in clamping engagement and an open position in which the grasping surfaces are spaced apart vertically.

21. In the instrument define din claim 20, the support arms being offset laterally and being movable relatively vertically past each other by manipulation of the handle end portions of the blades.

22. In the instrument defined in claim 21, the first grasping surface including a marginal portion offset laterally from the support arm of the first blade, and the second grasping surface of the second blade being positioned for engagement against said marginal portion.

* * * * *